United States Patent [19]

Wroblowsky et al.

[11] Patent Number: 5,710,303
[45] Date of Patent: *Jan. 20, 1998

[54] PROCESS FOR THE PREPARATION OF ALKOXYTRIAZOLINONES

[75] Inventors: Heinz-Jürgen Wroblowsky, Langenfeld; Klaus König, Odenthal, both of Germany

[73] Assignee: Bayer Aktiengesellschaft, Leverkusen, Germany

[*] Notice: The term of this patent shall not extend beyond the expiration date of Pat. No. 5,597,939.

[21] Appl. No.: 723,706

[22] Filed: Sep. 30, 1996

Related U.S. Application Data

[62] Division of Ser. No. 528,583, Sep. 15, 1995, Pat. No. 5,599,945.

[30] Foreign Application Priority Data

Sep. 23, 1994 [DE] Germany ............... 44 33 967.4

[51] Int. Cl.⁶ ............................................. C07C 275/70
[52] U.S. Cl. ............................................. 558/8
[58] Field of Search ..................... 560/159, 22; 558/8

[56] References Cited

U.S. PATENT DOCUMENTS

| | | | |
|---|---|---|---|
| 5,356,865 | 10/1994 | Müller et al. | 504/273 |
| 5,488,028 | 1/1996 | Haas et al. | 504/273 |
| 5,534,486 | 7/1996 | Müller et al. | 504/273 |
| 5,552,369 | 9/1996 | Findelsen et al. | 504/273 |
| 5,554,761 | 9/1996 | Haas et al. | 548/263.6 |
| 5,597,939 | 1/1997 | Müller et al. | 558/8 |

FOREIGN PATENT DOCUMENTS

| | | |
|---|---|---|
| 0477646 | 4/1992 | European Pat. Off. |
| 0507171 | 10/1992 | European Pat. Off. |
| 1940367 | 2/1971 | Germany |
| 9408979 | 4/1994 | WIPO |

OTHER PUBLICATIONS

P. Guha, et al., J. Indian Chem. Soc., vol. 6, pp. 565–575, (1929).
G. Zinner, et al., Arch. Pharm., vol. 307, pp. 889–891, (1974).
Chemical Abstracts, vol. 82, abstract No. 86060x, p. 494, abstract of Arch. Pharm., vol. 307, pp. 889–891, (1975).
P.R. Atkins, et al., J.C.S. Perkins I, pp. 2644–2656, (1973).
F. Arndt, et al., Rev. Fac. Sci. Istanbul, vol. 13A, pp. 127–144, (1948).
Chemical Abstracts, vol. 42, abstract No. 8190d, abstract of Rev. Fac. Sci. Istanbul, vol. 13A, (1948).
G. Zinner, et al., Arch. Pharm., vol. 307 (11), pp.889–891 (in German), (1974).
English translation of G. Zinner, et al., Arch. Pharm., vol. 307 (11), pp. 889–891 (in German), (1974).
CA 86060x Reaction of . . . hydrazides. Zinner et al., p. 494, 1975.

*Primary Examiner*—Joseph McKane
*Attorney, Agent, or Firm*—Sprung Kramer Schaefer & Briscoe

[57] ABSTRACT

Alkoxytriazolinones of the formula (I),

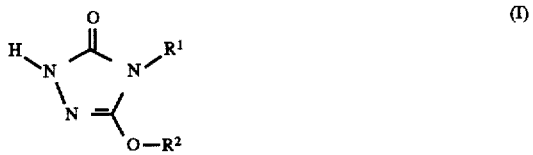

are obtained in good yields and in high purity by reacting iminocarbonic diesters (II) with carbazinic esters (III)

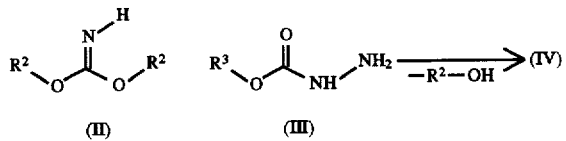

at $-20°$ C. to $+120°$ C. (1st step) and subjecting the semicarbazide derivatives (IV) formed in this process with elimination of $R^2$—OH

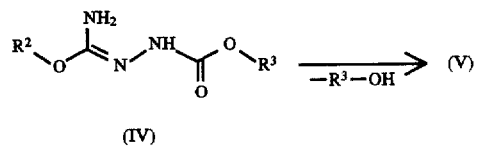

to a cyclizing condensation reaction in the presence of a base at $20°$ C. to $150°$ C. with elimination of $R^3$—OH, if appropriate (2nd step) and, finally, by reacting the resulting 5-alkoxytriazolinones of the formula (V) [=formula (I) where $R^1$=H] with an alkylating agent of the formula $R^1$—X (VI) at $0°$ C. to $150°$ C., if appropriate in the presence of a base.

1 Claim, No Drawings

PROCESS FOR THE PREPARATION OF ALKOXYTRIAZOLINONES

This application is a divisional of application Ser. No. 08/528,583, filed on Sep. 15, 1995, now U.S. Pat. No. 5,599,945.

The invention relates to a new process for the preparation of alkoxytriazolinones, most of which are known and which can be used as intermediates for the preparation of agrochemical active compounds, it also being possible for the process to be carried out on an industrial scale.

Alkoxytriazolinones and a plurality of methods for their preparation are already known (cf. J. Indian Chem. Soc. 6 (1929), 565–575; J. Chem. Soc. Perkin I 1973, 2644–2646; Arch. Pharm. 307 (1974), 889–891; EP-A477646; EP-A 507171). However, these known synthetic methods give alkoxytriazolinones only in highly unsatisfactory yields.

It is furthermore known to form 5-methoxy-4-methyl-2,4-dihydro-3H-1,2,4-triazol-3-one by methylating urazole or 4-methylurazole with diazomethane ($CH_2N_2$) (cf. F. Arndt et al., Rev. Fac. Sci. Istanbul 13A, pp. 127–144 (1948)); while this method affords high yields of the triazolinone, it cannot be carried out on an industrial scale.

It has now been found that alkoxytriazolinones of the general formula (I)

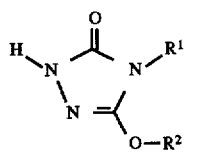

in which
$R^1$ represents in each case optionally substituted alkyl, alkenyl, alkinyl, cycloalkyl, cycloalkylalkyl, aryl or arylalkyl and
$R^2$ represents in each case optionally substituted alkyl, alkenyl, alkinyl, cycloalkyl, cycloalkylalkyl, aryl or arylalkyl, are obtained in very good yields and in high purity when iminocarbonic diesters of the general formula (II)

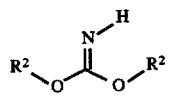

in which
$R^2$ has the abovementioned meaning are reacted with carbazinic esters of the general formula (III)

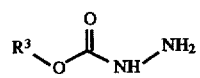

in which
$R^3$ represents in each case optionally substituted alkyl, aryl or arylalkyl, if appropriate in the presence of a reaction auxiliary and if appropriate in the presence of a diluent at temperatures between −20° C. and +120° C. ("first reaction step") and the semicarbazide derivatives formed in this process of the general formula (IV)

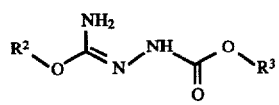

in which
$R^2$ and $R^3$ have the abovementioned meaning, —and/or the corresponding tautomeric compounds—are subjected to a cyclizing condensation reaction, at temperatures between 20° C. and 150° C., if appropriate after intermediate isolation, if appropriate in the presence of a base and if appropriate in the presence of a diluent ("second reaction step") and finally reacting the resulting alkoxytriazolinones of the general formula (V)

in which
$R^2$ has the abovementioned meaning —and/or the corresponding, tautomeric compounds—with an alkylating agent of the general formula (VI)

in which
X represents halogen or the groups $—O—SO_2—O—R^1$ or $—O—CO—O—R^1$ and
$R^1$ has the abovementioned meaning, at temperatures between 0° C. and 150° C., if appropriate in the presence of a base and if appropriate in the presence of a diluent ("third reaction step").

Surprisingly, the alkoxytriazolinones of the general formula (I) can be obtained in considerably higher yields by the process according to the invention than by most of the known synthetic methods. Compared with the "diazomethane method" (F. Arndt et al., l.c.) the decisive advantage of the process according to the invention is that it can also be carried out on an industrial scale.

What is to be regarded as particularly surprising is the fact that the alkylation of the compound of the formula (V) in the third step proceeds with high selectivity on the N atom in the 4-position and not on any of the other N atoms or on the carbonyl oxygen.

In this context, the terms "alkylation" and "alkylating agent" (VI) are used in this context as generic terms and thus expressly include all possibilities which arise from the above definition of $R^1$ (i.e. in addition to $R^1$=alkyl, cycloalkyl and arylalkyl, $R^1$ is also alkenyl, alkynyl, cycloalkyl and aryl).

Since the starting substances required of the formulae (II) and (III) are inexpensive chemicals which are relatively simple to prepare and since the reactions according to the invention proceed smoothly and in high yields, the process according to the invention represents a valuable enrichment of the prior art.

In one possible embodiment of the process according to the invention, all steps can be carried out as a "one-pot reaction", i.e. without intermediate isolation of the intermediates.

The invention preferably relates to the preparation of compounds of the formula (I) in which
$R^1$ represents alkyl, alkenyl or alkinyl, each of which has up to 6 carbon atoms and each of which is optionally substituted by cyano, halogen or $C_1$–$C_4$-alkoxy, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen or $C_1$–$C_4$-alkyl, or represents aryl or arylalkyl, each of which has 6 or 10 carbon atoms in the aryl moiety and, if appropriate, 1 to 4 carbon atoms in the alkyl moiety and each of which is optionally substituted by carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl, and $R^2$ represents alkyl, alkenyl or alkinyl, each of which has up to 6 carbon atoms and each of which is optionally substituted by halogen or $C_1$–$C_4$-alkoxy, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen or $C_1$–$C_4$-alkyl, or represents aryl or arylalkyl, each of which has 6 or 10 carbon atoms in the aryl moiety and, if appropriate, 1 to 4 carbon atoms in the alkyl moiety and each of which is optionally substituted by carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl.

The invention particularly relates to the preparation of compounds of the formula (I) in which $R^1$ represents methyl, ethyl, n- or i- propyl or n-, i-, s- or t-butyl, each of which is optionally substituted by cyano, fluorine, chlorine and/or bromine, methoxy or ethoxy, or represents propenyl, butenyl, propinyl or butinyl, each of which is optionally substituted by cyano, fluorine, chlorine and/or bromine, or represents cyclopropyl, cyclobutyl or cyclopropylmethyl, each of which is optionally substituted by fluorine, chlorine, bromine, methyl or ethyl, or represents phenyl or benzyl, each of which is optionally substituted by cyano, fluorine, chlorine, bromine, methyl, ethyl, trifluoromethyl, methoxy, ethoxy, difluoromethoxy, trifluoromethoxy, methoxycarbonyl or ethoxycarbonyl, and $R^2$ represents methyl, ethyl, n- or i- propyl or n-, i-, s- or t-butyl, each of which is optionally substituted by fluorine, chlorine and/or bromine, methoxy or ethoxy, or represents propenyl, butenyl, propinyl or butinyl, each of which is optionally substituted by cynano, fluorine, chlorine and/or bromine, or represents cyclopropyl or cyclopropylmethyl, each of which is optionally substituted by fluorine, chlorine, methyl or ethyl, or represents phenyl or benzyl, each of which is optionally substituted by cyano, fluorine, chlorine, bromine, methyl, ethyl, trifluoromethyl, methoxy, ethoxy, difluoromethoxy, trifluoromethoxy, methoxycarbonyl or ethoxycarbonyl.

If, for example, dimethyl imino-carbonate and ethyl carbazinate as well as methyl bromide are used as starting substances, the course of the reaction in the process according to the invention can be outlined by the following equation:

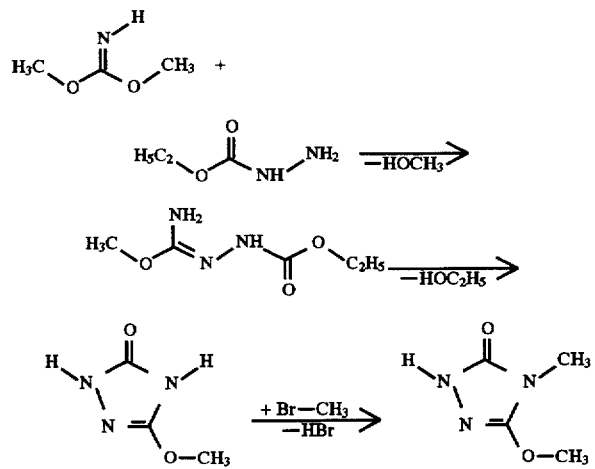

Formula (II) provides a general definition of the iminocarbonic diesters to be used as starting substances in the process according to the invention for the preparation of the compounds of the general formula (I). In formula (II), $R^2$ preferably, or in particular, has the meaning which has already been mentioned above in connection with the description of the compounds of the formula (I) preferred or particularly preferred for $R^2$.

The starting substances of the formula (II) are known and/or can be prepared by processes known per se (cf. Chem. Ber. 46 (1913), 2447; J. Prakt. Chem. 315 (1973), 640–648; DE-A 1518230; DE-A 4123608).

Formula (III) provides a general definition of the carbazinic esters furthermore to be used as starting substances in the process according to the invention. In formula (III), $R^3$ preferably represents $C_1$–$C_4$-alkyl which is optionally substituted by $C_1$–$C_4$-alkoxy, or represents phenyl or benzyl, in particular methyl, ethyl, methoxyethyl, ethoxyethyl or phenyl.

The starting substances of the formula (III) are known chemicals for organic synthesis.

The semicarbazide derivatives of the formula (IV) which are formed as intermediates in the first step of the process according to the invention are new, with the exception of the compounds in which $R^2$ represents phenyl and $R^3$ represents methyl or tert-butyl;

$R^2$ represents 2.2.2-trichloroethyl and $R^3$ represents methyl, ethyl or tert-butyl; and $R^2$ represents 2.2.2-trifluoroethyl and $R^3$ represents methyl, ethyl or tert-butyl.

These eight semicarbazide derivatives, prepared by a different process, have previously been described (cf. G. Zinner, Arch. Pharm. 307, p. 889–891 (1974)).

The 5-alkoxytriazolinones of the formula (V) which are formed as intermediates in the second step of the process according to the invention are also new, with the exception of the compounds in which $R^2$ represents methyl, ethyl, phenyl, 3-methylphenyl, 2,4-dimethylphenyl or 3-tert-butylphenyl.

These six alkoxytriazolinones, prepared in each case by other, different processes, have previously been described (cf. J. Chem. Soc., Perkin Trans. I, p. 2644–2646 (1973) for $R^2$=$CH_3$; Arch. Pharm. 307, p. 889–891 (1974) for $R^2$=$C_2H_5$; DE-A-19 40 367 for $R^2$=$C_6H_5$ and substituted phenyl as indicated above).

The new semicarbazide derivatives of the formula (IV) and the new alkoxytriazolinones of the formula (V) as such are also a subject of the present invention.

Formula (VI) provides a general definition of the alkylating agents furthermore to be used as starting substances in the process according to the invention. In formulae (VI), $R^1$ preferably, or in particular, has the meaning which has already been mentioned above in connection with the description of the compounds of the formula (I) as being preferred, or particularly preferred, for $R^1$.

The starting substances of the formula (VI) are known chemicals for organic synthesis.

Diluents which are suitable for carrying out the process according to the invention are (in all reaction steps) the customary organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, tetrachloromethane; ethers such as diethyl ether, diisopropyl ether, dioxane, tetrahydrofuran or ethylene glycol dimethyl ether or ethylene glycol diethyl ether; ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methyl-pyrrolidone or hexamethylphosphoric triamide; esters such as methyl acetate or ethyl acetate, sulphoxides such as dimethyl sulphoxide, alcohols such as methanol, ethanol, n- or i-propanol, n-, i-, s- or t-butanol, ethylene glycol monomethyl ether, ethylene glycol monoethyl ether, diethylene glycol monomethyl ether, diethylene glycol monoethyl ether, mixtures of these with water, or pure water.

Alcohols such as methanol, ethanol or n- or i-propanol are particularly preferred as diluents in the first step.

The first step of the process according to the invention is preferably carried out in the presence of a suitable reaction auxiliary. Suitable reaction auxiliaries are preferably protonic acids such as, for example, hydrochloric acid, sulphuric acid, phosphoric acid, carbonic acid, acetic acid, propionic acid, pivalic acid, methanesulphonic acid, benzoic acid, benzenesulphonic acid and p-toluenesulphonic acid, if appropriate also polymeric acids or acidic ion exchangers.

Particularly preferred reaction auxiliaries in the first steps of the process according to the invention are pivalic acid, acetic acid and (aqueous) hydrochloric acid.

The second and third steps of the process according to the invention are carried out preferably in the presence of a base. Suitable bases are all the conventional inorganic or organic bases. These include, for example, the hydrides, hydroxides, amides, alcoholates, acetates, carbonates or hydrogen carbonates of alkaline earth metals or alkali metals such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also basic organic nitrogen compounds such as trimethylamine, triethylamine, tributylamine, N,N-dimethylaniline, N,N-dimethyl-benzylamine, pyridine, N-methylpiperidine, N,N-dimethylaminopyridine, 5-ethyl-2-methyl-pyridine, diazabicyclooctane (DABCO), diazabicyclononene (DBN) or diazabicycloundecene (DBU).

Particularly preferred as bases in the second step of the process according to the invention are alkali metal hydroxides, such as sodium hydroxide or potassium hydroxide, alkali metal alcoholates, such as sodium methylate or sodium ethylate, or alkali metal carbonates, such as sodium carbonate or potassium carbonate.

When carrying out the first step of the process according to the invention, the reaction temperatures can be varied within a substantial range. In general, the process is carried out at temperatures between −20° C. and +120° C., preferably at temperatures between −10° C. and 90° C., in particular at temperatures between 0° C. and 60° C.

When carrying out the second step of the process according to the invention, the reaction temperatures can be varied within a substantial range. In general, the process is carried out at temperatures between 20° C. and 150° C., preferably at temperatures between 30° C. and 90° C., in particular at temperatures between 40° C. and 80° C.

When carrying out the third step of the process according to the invention, the reaction temperatures can be varied within a substantial range. In general, the process is carried out at temperatures between 0° C. and 150° C., preferably at temperatures between 30° C. and 90° C., in particular at temperatures between 40° C. and 80° C.

All steps of the process according to the invention are generally carried out under atmospheric pressure. However, it is also possible to carry out the process under elevated or reduced pressure, in general between 0.1 bar and 10 bar.

For carrying out the process according to the invention for the preparation of the compounds of the formula (I), 0.5 to 1.2 mol, preferably 0.8 to 1.1 mol, of carbazinic ester of the formula (III) and, 1.0 to 3.0 mol, preferably 1.05 to 1.50 mol, of alkylating agent of the formula (VI) are generally employed per mole of iminocarbonic diester of the formula (II).

In a preferred embodiment of the process according to the invention, the starting substances of the formula (II) and of the formula (III) and, if appropriate, a reaction auxiliary are mixed in a suitable diluent and stirred at the temperature required until virtually no starting material is present. The intermediate of the formula (IV) can then be isolated in the customary manner, for example by concentrating the mixture, digesting the residue with an organic solvent, such as, for example, methyl t-butyl ether, and filtering with suction. Alternatively, the intermediate of the formula (IV) can be treated with a base—if appropriate dissolved in one of the abovementioned diluents—and the mixture stirred at the temperature required for cyclizing condensation until the reaction has ended, without intermediate isolation. Before carrying out the last reaction step, it is preferred not to isolate the intermediate of the formula (V). It can, however, be isolated—if desired—for example by concentrating the mixture, taking up the residue in saturated aqueous sodium chloride solution, treating the mixture with an approximately equimolar amount of an acid such as, for example, hydrochloric acid, subjecting the mixture to filtration with suction and drying the solid product. To alkylate the resulting product, it is preferably taken up in one of the abovementioned solvents, and the mixture is treated with a base and an alkylating agent of the formula (VI) and stirred at the temperature required until the reaction has ended.

Alternatively, the intermediate of the formula (IV) can be reacted directly in a one—pot process by alkaline ring closure and, possibly after a solvent exchange, with an alkylating agent (VI) to give the alkoxytriazolinone (I), after isolation.

Alternatively, the entire synthetic sequence can also be carried out without isolating the intermediates.

Working-up to isolate the products of the formula (I) can be effected by customary methods. For example, the mixture is filtered and the filtrate concentrated, the residue is taken up in an organic solvent such as, for example, methylene chloride, and the mixture is filtered over silica gel. After the solvent has been removed carefully by distillation under reduced pressure, the product of the formula (I) is then obtained as a residue.

Alternatively, the reaction mixture can be heated to reflux temperature in the respective solvent after the alkylation reaction has taken place and the inorganics can be separated off by hot filtration. By cooling the filtrate, which is optionally first concentrated more strongly by partially distilling off the solvent, the products (I) are obtained as a precipitate, which is filtered off with suction and dried.

The compounds of the formula (I) to be prepared by the process according to the invention can be used as intermediates for the preparation of herbicidally active compounds (cf. EP-A 477646 and EP-A 507171).

PREPARATION EXAMPLES

Example 1

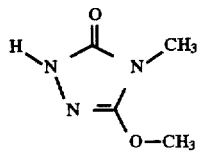

Steps 1 and 2

53.6 g (0.5 mol) of ethyl carbazinate are dissolved in 100 ml of methanol and, after 10 g (0.01 mol) of pivalic acid have been added, 213 g of a 23% strength solution of dimethyl iminocarbonate (0.55 mol) in methanol are slowly metered in at 0° C. The mixture is stirred for 2 hours at 0° C. and for a further 6 hours at 20° C. 90 g of a 30% strength solution of sodium methanolate (0.5 mol) in methanol are then added and the reaction mixture is stirred for 15 hours at 55° C. It is subsequently concentrated, the residue is taken up in 150 ml of saturated aqueous sodium chloride solution, and 0.5 mol of concentrated hydrochloric acid are added dropwise at 0° C. After 10 minutes at 0° C., the mixture is filtered with suction and the solid obtained dried.

38.9 g (68% of theory) of 5-methoxy-2,4-dihydro-3H-1, 2,4-triazol-3-one of melting point 220° C. are obtained (after determining the pure substance content).

Step 3

10.0 g (87 mmol) of 5-methoxy-2,4-dihydro-3H-1,2,4-triazol-3-one are dissolved in 120 ml of acetonitrile and, after 12.6 g (91 mmol) of potassium carbonate have been added, 11.5 g (91 mmol) of dimethyl sulphate are added dropwise at 55° C. The reaction mixture is stirred for 2 hours at 55° C. and then filtered. The filtrate is concentrated, the residue is dissolved in methylene chloride, and the mixture is filtered over silica gel. The solvent is carefully removed from the filtrate by distillation under reduced pressure.

The residue is recrystallized from water.

8.4 g (73% of theory—based on the starting material employed in the third step) of 5-methoxy-4-methyl-2,4-dihydro-3H-1,2,4-triazol-3-one of melting point 148° C. are obtained.

Example 2

(Third Step Only)

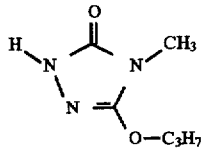

10.0 g (70 mmol) of 5-propoxy-2,4-dihydro-3H-1,2,4-triazol-3-one (cf. example V-1) are dissolved in 120 ml of acetonitrile and, after 10.1 g (73 mmol) of potassium carbonate have been added, 9.2 g (73 mmol) of dimethyl sulphate are added dropwise at 55° C. The reaction mixture is stirred for 6 hours at 55° C. and then filtered. The filtrate is concentrated, the residue dissolved in methylene chloride and the solution filtered over silica gel. The solvent is carefully removed from the filtrate by distillation under reduced pressure.

10.5 g (90% of theory) of 4-methyl-5-propoxy-2,4-dihydro-3H-1,2,4-triazol-3-one are obtained as an amorphous product.

Example 3

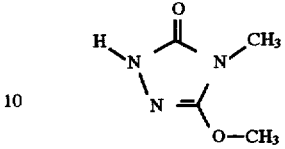

("One-pot method")

42.8 g (0.4 mol) of ethyl carbazinate are introduced into 40 ml of methanol and, after 128.4 ml of a methanolic solution of 0.44 mol of dimethyl iminocarbonate have been added, cooled to 0° C. After an addition of 0.8 ml of concentrated hydrochloric acid (0.008 mol of HCl), the mixture is stirred for 2 hours at 0° C. and then another 24 hours at 20° C. 89.5 g of a methanolic solution of sodium methylate (0.42 mol of NaOCH$_3$) are subsequently metered in, and the mixture is stirred for 12 hours at 55° C. to 60° C. It is then cooled to 20° C., and 37.9 g (0.4 mol) of dimethyl sulphate are metered in dropwise. The reaction mixture is stirred for 2 hours at 40° C., a further 3.8 g (0.04 mol) of dimethyl sulphate are added, and stirring is continued for 2 hours at 40° C. The mixture is then concentrated under a water pump vacuum, the residue taken up in 120 ml of water and the mixture acidified using concentrated hydrochloric acid in an ice-bath. The product obtained as crystals is isolated by filtration with suction.

33.7 g of 5-methoxy-4-methyl-2,4-dihydro-3H-1,2,4-triazol-3-one (content: 90%, yield: 59% of theory over all steps) are obtained.

The following Examples 4 to 6 show how the second and third stage in the one-pot process are carried out:

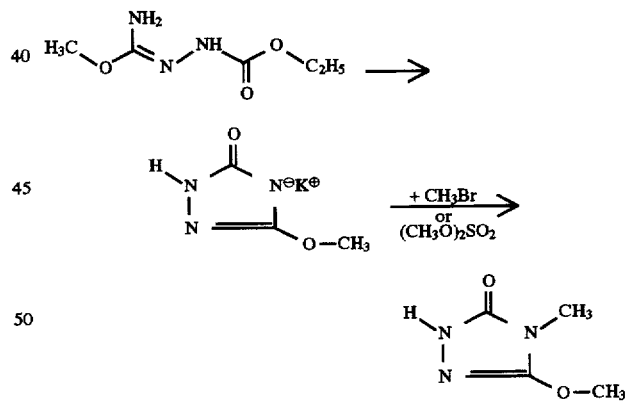

Example 4

Methylation With Methyl Bromide 50 g (0.306 mol) of ethyl N'-(α-amino-α-methoxy-methylene)-hydrazine-N-carboxylate (content: 98.5%) are added to a solution of 20.4 g (0.321 mol) of 88% strength potassium hydroxide in 220 ml of methanol and the mixture is stirred overnight at 55° C. The methanol is then removed in vacuo, the residue is taken up using 300 ml of propionitrile and cooled to −10° C., 32 g (0.336 mol) of methyl bromide are condensed in and the mixture is stirred at 55° C. under autogenous pressure for 6 hours. The pressure vessel is then let down and the reaction mixture is heated to reflux temperature and filtered off hot from the insoluble potassium bromide. The filtrate is concentrated to about 100 ml and cooled to −15° C.; the product which is deposited during the course of this is filtered off and dried in vacuo.

28.8 g (72% of theory) of 5-methoxy-4-methyl-2,4-dihydro-3H-1,2,4-triazol-3-one (content according to HPLC against standard: 99%) of melting point 146° C. are obtained.

Example 5

Methylation With Methyl Bromide 70 g (0.428 mol) of ethyl N'-(α-amino-α-methoxy-methylene)-hydrazine-N-carboxylate (content: 98.5%) are added to a solution of 28.4 g (0.446 mol) of 88% strength potassium hydroxide in 300 ml of methanol and the mixture is stirred overnight at 55° C. The solvent is then removed in vacuo, the residue is taken up in 250 ml of methyl isobutyl ketone and cooled to −10° C., 44.4 g (0.467 mol) of methyl bromide are condensed in and the mixture is stirred at 55° C. under autogenous pressure for 6 hours.

To determine the yield, after letting down the pressure vessel the mixture is evaporated to dryness and the crude product (weight: 103.6 g) is pulverized in a mortar.

Content of 5-methoxy-4-methyl-2,4-dihydro-3H-1,2,4-triazol-3-one against standard: 47% by weight (corresponds to a yield of 89% of theory); Content of KBr: 45.2% by weight.

Example 6

Methylation With Dimethyl Sulfate 50 g (0.306 mol) of ethyl N'-(α-amino-α-methoxy-methylene)hydrazine-N-carboxylate (content: 98.5%) are added to a solution of 20.4 g (0.321 mol) of 88% strength potassium hydroxide in 250 ml of methanol and the mixture is stirred at 55° C. overnight. It is then concentrated, the residue is taken up in 270 ml of methyl isobutyl ketone, and 40.5 g (0.321 mol) of dimethyl sulfate are added dropwise in the course of 2 hours. After addition is complete, the mixture is additionally stirred at 55° C. for a further 2 hours and then concentrated to about a third of the original volume and the solids are filtered off. To remove the inorganics from the filter residue, the solids are heated to reflux with 200 ml of propionitrile and filtered off hot. The filtrate is evaporated and the solid residue is dried in vacuo.

29.2 g (69.5% of theory) of 5-methoxy-4-methyl-3H-1,2,4-triazol-3-one are obtained (content: 94%).

INTERMEDIATES OF THE FORMULA (IV)

Example (IV-1)

$$H_3C\diagdown_O\diagup^{NH_2}_{\diagdown N\diagup^{NH}\diagdown_{\underset{O}{C}}\diagdown_O\diagdown C_2H_5}$$

21.1 g (0.2 mol) of ethyl carbazinate are introduced into 20 ml of methanol and, after 61.3 ml of a methanolic solution of dimethyl iminocarbonate with a diester content of 305 g/l (=0.21 mol of diester) have been added, the mixture is cooled to 0° C. 0.4 ml of concentrated hydrochloric acid (0.004 mol of HCl) are then added and the mixture is stirred for 6 hours at 0° C. and for a further 15 hours at 20° C. After a further 2.9 ml of the methanolic solution of dimethyl iminocarbonate have been added, the mixture is stirred for a further 6 hours at 20° C. It is then concentrated under a water pump vacuum, the residue is stirred with 220 ml of t-butyl methyl ether, and the crystalline product is isolated by filtration with suction.

30.1 g (90% of theory) of ethyl N'-(α-amino-α-methoxy-methylene)-hydrazine-N-carboxylate are obtained (content: 96.1%).

$^1$H NMR (dimethyl sulphoxide-D$_6$): 1.165 ppm (3H, triplet); 3.573 ppm (3H, singlet); 3.994 ppm (2H, quartet); 5.887 ppm (2H, singlet); 8.475 ppm (1H, singlet).

Example (IV-2)

$$H_3C\diagdown_O\diagup^{NH_2}_{\diagdown N\diagup^{NH}\diagdown_{\underset{O}{C}}\diagdown_O\diagdown C_2H_5}$$

21.1 g (0.2 mol) of ethyl carbazinate are introduced into 20 ml of methanol and, after 61.3 ml of a methanolic solution of dimethyl iminocarbonate with a diester content of 305 g/l (=0.21 mol of diester) have been added, the mixture is cooled to 0° C. 0.24 g (0.004 mol) of acetic acid in 2 ml of methanol are then added dropwise. The mixture is stirred for 6 hours at 0° C. and for a further 15 hours at 20° C. It is then concentrated under a water pump vacuum, the residue is stirred with t-butyl methyl ether, and the crystalline product isolated by filtration with suction.

30.8 g (93% of theory) of ethyl N'-(α-amino-α-methoxy-methylene)-hydrazine-N-carboxylate (content: 97.5%) of melting point 134° C. are obtained.

Example (IV-3)

$$n\text{-}H_7C_3\diagdown_O\diagup^{NH_2}_{\diagdown N\diagup^{NH}\diagdown_{\underset{O}{C}}\diagdown_O\diagdown C_2H_5}$$

6.0 g (0.041 mol) of dipropyl iminocarbonate and 4.07 g (0.038 mol) of ethyl carbazinate are dissolved in 20 ml of methanol, and a solution of 0.19 g (0.0019 mol) of pivalic acid in 2 ml of methanol is added dropwise at 20° C. The mixture is stirred for a further 15 hours at 20° C. It is then concentrated under a water pump vacuum, the residue is stirred with 30 ml of t-butyl methyl ether, and the crystalline product is isolated by filtration with suction.

5.54 g (75% of theory) of ethyl N'-(α-amino-α-n-propoxy-methylene)-hydrazine-N-carboxylate (content: 96.7%) of melting point 100° C. are obtained.

Example (IV-4)

$$n\text{-}H_7C_3\diagdown_O\diagup^{NH_2}_{\diagdown N\diagup^{NH}\diagdown_{\underset{O}{C}}\diagdown_O\diagdown C_2H_5}$$

26.8 g (0.25 mol) of ethyl carbazinate (content: 97%) and 48.4 g (0.30 mol) of di-n-propyl iminocarbonate (content: 90%) are initially introduced into 120 ml of n-propanol at room temperature, and a solution of 1.53 g (0.015 mol) of pivalic acid in 40 ml of n-propanol is added dropwise in the course of 1.5 hours. After addition is complete, the mixture is additionally stirred overnight and a further 4.8 g (0.03 mol) of dipropyl iminocarbonate and 0.5 g of pivalic acid are then added to the reaction mixture. After stirring at room temperature for a further 4 hours, the mixture is concentrated, the residue is treated with 250 ml of petroleum ether and stirred at room temperature for 1.5 hours, and the product is filtered off.

41.75 g (88.1% of the theory) of ethyl N'-(α-amino-α-n-propoxymethylene)hydrazine-N-carboxylate (content: 98.7%) are obtained.

INTERMEDIATES OF THE FORMULA (V)

Example (V-1)

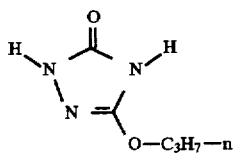

6.82 g (0.0349 mol) of ethyl N'-(α-amino-α-n-propoxymethylene)-hydrazine-N-carboxylate are dissolved in 40 ml of methanol, and 7.6 g of a solution of 0.0366 mol of sodium methylate in methanol is added dropwise at 20° C. The mixture is stirred for 12 hours at 55° C. It is then concentrated under a water pump vacuum, the residue is taken up in 12 ml of water, and the pH is brought to 6 by adding concentrated hydrochloric solution with ice-cooling. The product obtained as crystals is isolated by filtration with suction.

3.47 g (69.5% of theory) of 5-propoxy-2,4-dihydro-3H-1,2,4-triazol-3-one of melting point 156° C. are obtained.

Example (V-2)

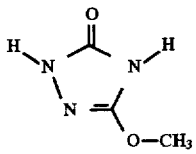

19.5 g (0.115 mol) of ethyl N'-(α-amino-α-methoxy-methylene)-hydrazine-N-carboxylate (content: 94.6%) are introduced into a mixture of 20 ml of methanol and 30 ml of water and, after 10.8 g of 45% strength aqueous sodium hydroxide solution have been added (0.12 mol of NaOH), the mixture is stirred for 16 hours at 55° C. It is then concentrated under a water pump vacuum, the residue is taken up in 30 ml of water, the mixture is acidified using concentrated hydrochloric acid with ice-cooling, and the product obtained as crystals is isolated by filtration with suction.

10.0 g (76% of theory) of 5-methoxy-2,4-dihydro-3H-1,2,4-triazol-3-one are obtained.

Example (V-3)

Stages 1 and 2 in the One-pot Process

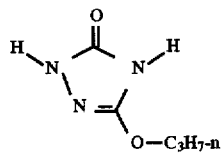

50 g (0.345 mol) of di-n-propyl iminocarbonate (content: 99.2%) and 33.7 g (0.314 mol) of ethyl carbazinate (content: 97%) are initially introduced into 130 ml of n-propanol, and a solution of 1.6 g (0.0157 mol) of pivalic acid in 20 ml of n-propanol is added dropwise at room temperature in the course of 1.5 hours. After addition is complete, the mixture is additionally stirred at room temperature overnight and 73.4 g (0.345 mol of NaOCH$_3$) of a methanolic solution of sodium methylate are then added dropwise; the reaction mixture is then additionally stirred at 55°–60° C. for 22 hours. The solvent is subsequently removed in vacuo and the residue is treated with 40 ml of ice-water and 160 ml of n-butyronitrile; this mixture is acidified with cooling by addition of concentrated hydrochloric acid and heated to 85° C., then the two phases are separated. The aqueous phase is treated a further two times (extracted) at 85° C. with 40 ml of n-butyronitrile each time, and the combined organic phases are washed with 15 ml of saturated sodium chloride solution and evaporated in vacuo. The residual solid is stirred with 300 ml of petroleum ether and the product is filtered off.

45.7 g (91.1% of theory, over the two stages, based on ethyl carbazinate employed) of 5-propoxy-2,4-dihydro-3H-1,2,4-triazol-3-one are obtained (content: 89.5%).

We claim:
1. The semicarbazide compounds

(a) ethyl N'-(α-amino-α-methoxy-methylene)-hydrazine-N-carboxylate

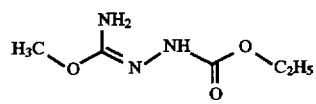

and (b) ethyl N'-(α-amino-α-propoxy-methylene)-hydrazine-N-carboxylate

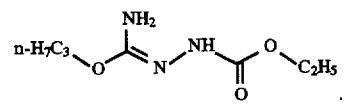

* * * * *